(12) United States Patent
Fabian et al.

(10) Patent No.: US 9,677,047 B2
(45) Date of Patent: Jun. 13, 2017

(54) HIGH SURFACE AREA SUBSTRATE FOR CELL CULTURE

(75) Inventors: Michelle Dawn Fabian, Horseheads, NY (US); Timothy Edward Myers, Painted Post, NY (US); Kyle Patrick Snyder, Horseheads, NY (US); Florence Verrier, Corning, NY (US)

(73) Assignee: Corning Incorporated, Corning, NY (US)

( * ) Notice: Subject to any disclaimer, the term of this patent is extended or adjusted under 35 U.S.C. 154(b) by 453 days.

(21) Appl. No.: 12/845,483

(22) Filed: Jul. 28, 2010

(65) Prior Publication Data

US 2012/0058556 A1 Mar. 8, 2012

Related U.S. Application Data

(60) Provisional application No. 61/308,101, filed on Feb. 25, 2010, provisional application No. 61/229,114, filed on Jul. 28, 2009.

(51) Int. Cl.
| | |
|---|---|
| *C12N 11/00* | (2006.01) |
| *C12N 11/14* | (2006.01) |
| *C12N 11/06* | (2006.01) |
| *C12N 5/02* | (2006.01) |
| *C12N 5/00* | (2006.01) |
| *C12N 5/0735* | (2010.01) |

(52) U.S. Cl.
CPC ......... *C12N 5/0075* (2013.01); *C12N 5/0606* (2013.01); *C12N 2533/30* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 5,512,474 A * | 4/1996 | Clapper et al. | 435/402 |
| 6,214,618 B1 | 4/2001 | Hillegas et al. | |
| 7,708,908 B2 * | 5/2010 | Kim et al. | 252/500 |
| 2003/0129130 A1 * | 7/2003 | Guire et al. | 424/1.11 |

FOREIGN PATENT DOCUMENTS

| | | | |
|---|---|---|---|
| WO | 8905150 | 6/1989 | |
| WO | 8905150 | 6/1998 | ............. A61K 37/02 |
| WO | 2007136354 A1 | 11/2007 | |

OTHER PUBLICATIONS

Midwood et al., Tissue repair and the dynamics of the extracellular matrix, The International Journal of Biochemistry & Cell Biology 36 (2004) 1031-1037.*

(Continued)

*Primary Examiner* — Reza Ghafoorian
(74) *Attorney, Agent, or Firm* — Susan S. Wilks; Keith M. Campbell

(57) ABSTRACT

A cell culture microcarrier includes (1) a polystyrene microcarrier base having a remnant of a carboxylic acid group, and (ii) a polypeptide conjugated to the base via the remnant of the carboxylic acid group. The polypeptide may contain a cell adhesive sequence, such as RGD. Cells cultured with such microcarriers exhibit peptide-specific binding to the microcarriers.

18 Claims, 4 Drawing Sheets

(56) References Cited

OTHER PUBLICATIONS

Mann et al., Modication of surfaces with cell adhesion peptides alters extracellular matrix deposition, Biomaterials 20 (1999) 2281-2286.*
Chen et al., Surface Functionalization of Polystyrene to Bind With FMRF Peptides for Novel Biocompatibility, Chinese Journal of Polymer Science vol. 28, No. 6, (2010), 895_902.*
Wu et al., Effects of -COOH Groups on Organic Particle Surface on Hydrous Alumina Heterogeneous Coating, Ind. Eng. Chem. Res. 2007, 46, 4363-4367.*
Barrilleaux et al., Review: Ex Vivo Engineering of Living Tissues with Adult Stem Cells, Tissue Engineering, vol. 12, No. 11, 2006.*
Carboxylic acids (Reference 1), downloaded from http://www.chem.uky.edu/courses/che232/FTL/c19.pdf on Feb. 26, 2014.*
Hatakeyama et al., Patterned biofunctional designs of thermoresponsive surfaces for spatiotemporally controlled cell adhesion, growth, and thermally induced detachment, Biomaterials 28 (2007) 3632-3643.*
Underwood et al., Effects of polystyrene surface chemistry on the biological activity of solid phase fibronectin and vitronectin, analysed with monoclonal antibodies, Journal of Cell Science 104, 793-803 (1993).*
Jocobson et la., Growth of endothelial and HeLa cells on a new multipurpose microcarrier that is positive, negative or collagen coated, Tissue & Cell, 1982, 14 (1) 69-83.*
Bo et al., Adherence and Proliferation of Endothelial Cells on Surface-Immobilized Albumin-Heparin Conjugate, Tissue Engineering vol. 4, No. 3. 1998.*
Underwood et al., Effects of polystyrene surface chemistry on the biological activity of solid phase fibronectin and vitronectin, analyzed with monoclonal antibodies, Journal of Cell Science 104, 793-803 (1993).*
Klee et al., Surface modification of poly(vinylidenefluoride) to improve the osteoblast adhesion, Biomaterials 24 (2003) 3663-3670.*
Corning, Corning® Cell Culture Surfaces: Standard Tissue Culture Treated Surface, by Corning downloaded from the URL www.corning.com/lifesciences/us_canada/en/technical_resources/surfaces/culture/stc_treated_polystyrene.aspx taken from the Web on May 11, 2015.*
Sasai et al., Introduction of carboxyl group onto polystyrene surface using plasma techniques, Surface & Coatings Technology 202 (2008) 5724-5727.*
Hersel et al., RGD modified polymers: biomaterials for stimulated cell adhesion and beyond, Biomaterials 24 (2003) 4385-4415.*
Sasai et al., Surface modification of polystyrene dishes using plasma techniques to enhance cell adhesion and proliferation, unpublished, downloadable from http://www.ispc-conference.org/ispcproc/ispc19/208.pdf as of May 12, 2015.*
Genbacev et al, Fertil. Steril. 83(5):1517-29, Apr. 29, 2005.
Goddard et al: Polymer surface modification for the attachment of bioactive compounds, Progress in Polymer Science, Pergamon Press, vol. 32, No. 7, Jul. 1, 2007 pp. 698-725.
Solohill microcarriers beads, Nov. 1, 2005.
Phillips B W et al: Attachment and growth of human embryonic stem cells on microcarriers. Journal of Biotechnology, vol. 138, No. 1-2, Nov. 6, 2008, pp. 24-32.
Wang at el: Acid and basic functionalities of nitrogen and carbon dioxide plasma-treated polystyrene. Surface and Interface Analysis, Jan. 31, 2005, vol. 37 pp. 348-355.
Koide et al, 1993, Chem. Pharm. Bull. 41(3):502-6.
Koide et al, 1993, Chem. Pharm. Bull 41(9):1596-1600.
Besse and Moroder, 1997, Journal of Peptide Science, vol. 3, 442-453.
Thompson 1998, Science, 282:1145.
Genbacev et al, Fertil. Steril. 83(5):1517-29.
Cowan et al, NEJM 350(13):1353-56, 2004.
Klimanskaya et al, Lancet, 365(9471):1636-41, 2005.
Takahashi et al, (2007) Cell 131(5):861.
Yu et al, (2007) Science 318:5858.
Holzapfel, Preparation of Fluorescent Carboxyl; Macromolecular Chemistry and Physics; 2005 206(24):2440-2449 (p. 2446; table3).

* cited by examiner 86333 86358

US 9,677,047 B2

HIGH SURFACE AREA SUBSTRATE FOR CELL CULTURE

CROSS-REFERENCE TO RELATED APPLICATIONS

This application claims the benefit of priority under 35 U.S.C. §119(e) of U.S. Provisional Application Ser. No. 61/308,101 filed on Feb. 25, 2010 which claims the benefit of priority under 35 U.S.C. §119(e) of U.S. Provisional Application Ser. No. 61/229,114 filed on Jul. 28, 2009.

FIELD

The present disclosure relates to cell culture microcarriers, and more particularly to synthetic, chemically-defined microcarriers.

SEQUENCE LISTING

This application contains a Sequence Listing electronically submitted via EFS-Web to the United States Patent and Trademark Office as text filed named "SP10-044_ SEQ_ LIST ST25.txt" having a size of 1 kb and created on Nov. 17, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Microcarriers provide an alternative for large-scale cell culture. Microcarriers are typically stirred in cell culture media and provide a very large surface to area ratio for cell growth. Microcarriers can provide substantially higher cell yields per culture volume relative to conventional equipment.

Some microcarriers have been prepared to present specific polypeptide sequences at the surface, which polypeptides are configured to provide specific interaction with adhesion receptors of the cells. Examples of such microcarriers include gelatin or collagen linked to dextran beads or to polystyrene beads. While having various advantages, such microcarriers are made of animal derived materials and are not suitable for culturing cells dedicated to cell therapies due to the risk of xenogenic contamination through, for example, pathogen proteins or viruses.

To solve this issue, recombinant proteins or polypeptides have been synthesized and coated onto microcarriers. While such microcarriers have the advantage of being free of animal derived components, they may not have several drawbacks. For example, the level of cell adhesion with some of these beads may not be sufficiently high for robust culture of some anchorage-dependent cells, particularly when serum free media is used. When serum-free media are used, the media do not provide adhesion proteins, which can bind to the microcarrier surface and thus facilitate binding of cells. The absence of serum especially presents problems when using cells that produce little extracellular matrix, such as certain stem cells, including embryonic stem cells.

BRIEF SUMMARY

Among other things, the present disclosure describes synthetic, chemically-defined microcarriers that may provide robust and selective binding of anchorage-dependent cells. The microcarriers may be formed from conjugation of a polypeptide to a carboxylic acid group attached to the surface of a polystyrene microcarrier base. The polypeptide may contain an RGD amino acid sequence for mediating bio-specific cell adhesion. As described herein, such microcarriers allow for selective adhesion of cells via the polypeptide with little or no non-selective binding. Accordingly, the microcarriers described herein may be used to culture anchorage dependent cells in a controlled manner. As also described herein, such microcarriers allow the specific attachment and cell growth of pluripotent stem cells, including human embryonic stem cells (hESC).

In various embodiments, after grafting the polypeptides to carboxylic acid groups attached to the microcarrier base, the remaining non-peptide conjugated carboxylic acid groups, or a portion thereof, are blocked via derivation with a low molecular weight amine monamine, such as ethanolamine. Such blocking converts highly hydrophilic carboxylic acid groups to less hydrophilic amide group, which may affect the ability and nature of the binding of certain cells to the microcarrier. Accordingly, the hydrophilic characteristics of the microcarrier can be readily tuned, as desired, to impact cell behavior, due to the percentage of COOH groups blocked and the nature of the monoamine used for blocking.

One or more embodiments of the microcarriers or methods described herein provide one or more advantages over prior microcarriers, methods for preparing microcarriers, or methods for culturing cells with microcarriers. For example, the microcarriers described herein are devoid of animal derived materials, which limits the risk of pathogen contamination. This is particularly relevant when the cultured cells are dedicated to cell-therapies. The microcarriers may be monolithic and not coated, and thus are not prone to delamination. Due to low levels of non-specific binding to the microcarrier base, bioselective cell attachment through receptor binding to polypeptides grafted to the microcarrier can occur. Such highly bioselective attachment may be beneficial for culturing primary cells, hepatocytes, and other cells, such as stem cells including embryonic stem cells. In addition to ready tuning of the hydrophilicity of the surface of the microcarrier, the polypeptide density can be tuned by derivation of the carboxylic acid groups of the microcarrier based. These and other advantages will be readily understood from the following detailed descriptions when read in conjunction with the accompanying drawings.

DETAILED DESCRIPTION

Figure 1:
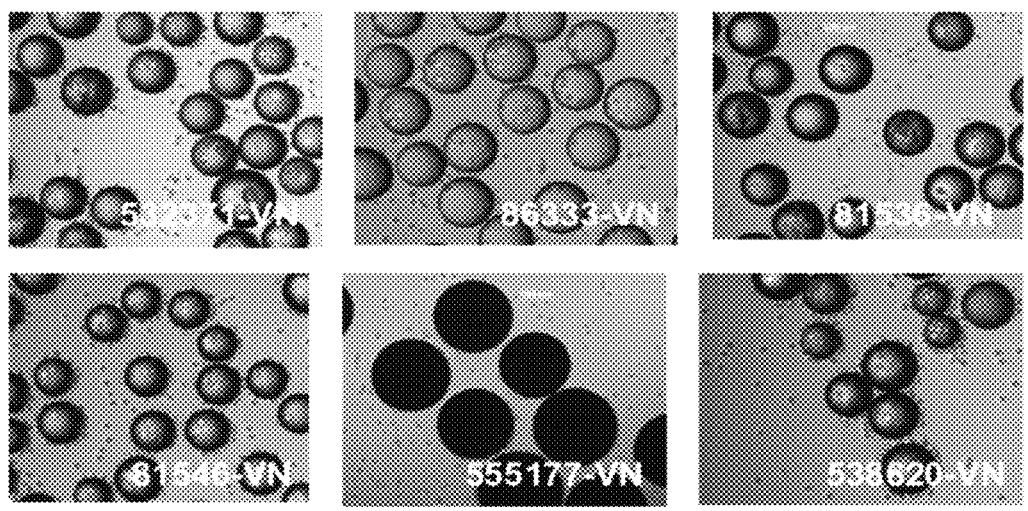
FIG. 1 shows images of HT1080 cells bound to polystyrene microcarriers having various length linkers and vitronectin (VN) peptide concentration.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "providing" an object or compounds means using, making or otherwise obtaining the object or compound.

Polypeptide sequences are referred to herein by their one letter amino acid codes and by their three letter amino acid codes. These codes may be used interchangeably.

As used herein, "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. Polypeptides may be of any suitable length, such as between three and 30 amino acids in length. Polypeptides may be acetylated (e.g. Ac-LysGlyGly) or amidated (e.g. SerLysSer-$NH_2$) to protect them from being broken down by, for example, exopeptidases. It will be understood that these modifications are contemplated when a sequence is disclosed.

As used herein, "microcarrier" means a small discrete particle for use in culturing cells and to which cells may attach. Microcarriers may be in any suitable shape, such as rods, spheres, and the like, and may be porous or non-porous.

A "microcarrier base", as used herein, means a microcarrier on which a polypeptide may be conjugated. For example, a microcarrier may be a polymeric bead, such as a polystyrene microbead.

As used herein, "polystyrene" means a polymer or copolymer formed from styrene monomers.

The present disclosure describes, inter alia, synthetic microcarriers for culturing cells. The microcarriers may be formed from conjugating polypeptides to carboxylic acid functional groups of a polystyrene microcarrier base. At least a portion of the carboxylic acid functional groups may be blocked by derivation with a low molecular weight monoamine. The resulting microcarriers provide polypeptide-selective binding with cells in culture.

1. Microcarrier

A microcarrier, as described herein, includes a microcarrier base and a polypeptide conjugated to the base. The microcarrier base may include polystyrene modifies to include a moiety to which a polypeptide may be grafted, either directly or indirectly.

In general, it is preferred that microcarriers have a density slightly greater than the cell culture medium in which they are to be suspended to facilitate separation of the microcarriers from the surrounding medium. In various embodiments, the microcarriers have a density of about 1.01 to 1.10 grams per cubic centimeter. Microcarriers having such a density should be readily maintained in suspension in cell culture medium with gentle stirring.

In addition, it is preferred that the size variation of the microcarriers is small to ensure that most, if not all, of the microcarriers can be suspended with gentle stirring. By way of example, the geometric size distribution of the microcarriers may be between about 1 and 1.4. Microcarriers may be of any suitable size. For example, microcarriers may have a diametric dimension of between about 20 microns and 1000 microns. Spherical microcarriers having such diameters can support the attachment of several hundred to thousands of cells per microcarrier.

A. Microcarrier Base

Any suitable polystyrene may be used to form the base. Polystyrene microcarriers may be formed via any suitable method or may be purchased from any number of commercial vendors, including Sigma-Aldrich, Polysciences, Inc., and Thermo Fischer Scientific.

To the extent that the beads or particles do not contain pendant carboxylic acid functional groups or other functional groups to which a polypeptide may be grafted, the beads or particles may be derivatized to include such groups. Any suitable method may be used to derivatize the particles to form a microcarrier base having such functional groups. For example, some methods for introducing carboxylate function into a polysaccharide backbone include reaction with chloroacetic acid, chloropropionic acid, bromohexanoic acid, succinic anhydride, glutaric anhydride, maleic anhydride, citraconic anhydride, or the like.

Examples of microcarrier bases that have carboxylic acid functional groups include Polybead® carboxylate microspheres from Polysciences, Inc.

In various embodiments, the content of carboxylic acid groups before peptide grafting is between about 0.1 millimoles per gram of microcarrier and about 5 millimoles per gram of microcarrier, such as between 0.1 millimoles per gram and 2 millimoles per gram, between 0.1 millimoles per gram and 1 millimoles per gram, between 0.1 millimoles per gram and 0.9 millimoles per gram, between 0.1 and 0.8 millimoles per gram, or between 0.1 millimoles per gram and 0.5 millimoles per gram.

A linker may separate the carboxylic acid group from the surface of the microcarrier base. The linker may be of any suitable length. In various embodiments, the linker may have a length of between 1 and 15. The linker may be an alkyl liner of between C1 and C15. Of course, one or more of the carbons may be replaced with O, N or the like. Some examples of linkers that may be used are (shown with attached COOH): ~$CH_2$—COOH~$CH_2$—$CH_2$—COOH, ~CH$_2$—CH$_2$—NH—CO—CH$_2$—CH$_2$—COOH, and ~CH$_2$—CH$_2$—O—CH$_2$—CH$_2$—NH—CO—CH$_2$—CH$_2$—COOH B. Conjugation of Polypeptide to Polymeric Microcarrier Base Any suitable polypeptide may be conjugated to a microcarrier base. Preferably, the polypeptide includes an amino acid capable of conjugating to microcarrier base; e.g. via a free carboxyl group of the base. By way of example, any native or biomimetic amino acid having functionality that enables nucleophilic addition; e.g. via amide bond formation, may be included in polypeptide for purposes of conjugating to the microcarrier base via a carboxylic acid group. Lysine, homolysine, ornithine, diaminoproprionic acid, and diaminobutanoic acid are examples of amino acids having suitable properties for conjugation to a carboxyl group of the microcarrier. In addition, the N-terminal alpha amine of a polypeptide may be used to conjugate to the carboxyl group, if the N-terminal amine is not capped. In various embodiments, the amino acid of polypeptide that conjugates with the microcarrier is at the carboxy terminal position or the amino terminal position of the polypeptide.

In numerous embodiments, the polypeptide, or a portion thereof, has cell adhesive activity; i.e., when the polypeptide is conjugated to the microcarrier base, the polypeptide allows a cell to adhere to the surface of the peptide-containing microcarrier. By way of example, the polypeptide may include an amino sequence, or a cell adhesive portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, BSP, or the like, or portions thereof. In various embodiments, polypeptide includes an amino acid sequence of ArgGlyAsp (RGD).

Microcarrier bases as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known polypeptides can be synthesized and applied to a microcarrier as described herein to allow the cells to be cultured on a synthetic surface having no or very few components of unknown origin or composition.

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

A linker or spacer, such as a repeating poly(ethylene glycol) linker or any other suitable linker, may be used to increase distance from polypeptide to surface of microcarrier. The linker may be of any suitable length. For example, if the linker is a repeating poly(ethylene glycol) linker, the linker may contain between 2 and 10 repeating ethylene glycol units. In some embodiments, the linker is a repeating poly(ethylene glycol) linker having about 4 repeating ethylene glycol units. All, some, or none of the polypeptides may be conjugated to a microcarrier base via linkers. Other potential linkers that may be employed include polypeptide linkers such as poly(glycine) or poly(β-alanine).

A polypeptide may be conjugated to the microcarrier at any density, preferably at a density suitable to support culture of undifferentiated stem cells or other cell types. Polypeptides may be conjugated to a microcarrier base at a density of between about 1 pmol per mm$^2$ and about 50 pmol per mm$^2$ of surface of the microcarrier. For example, the polypeptide may be present at a density of greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface of the microcarrier. It will be understood that the amount of polypeptide present can vary depending on the composition of the microcarrier base (e.g., the density of pendant carboxylic acid groups), the size of the microcarrier base and the nature of the polypeptide itself.

A polypeptide may be conjugated to the polymerized microcarrier via any suitable technique. A polypeptide may be conjugated to a polymerized microcarrier via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the microcarrier base to produce amine reactive NHS esters. EDC reacts with a carboxyl group of the microcarrier base to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two step procedure. Following activation of the microcarrier base, the polypeptide may then be added and the terminal amine of the polypeptide can react with the amine reactive ester to form a stable amide bond, thus conjugating the polypeptide to the microcarrier base. When EDC/NHS chemistry is employed to conjugate a polypeptide to the microcarrier, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide to microcarrier. Linkers or spacers, such as poly(ethylene glycol) linkers (e.g., available from Quanta BioDesign, Ltd.) with a terminal amine may be added to the N-terminal amino acid of polypeptide. When adding a linker to the N-terminal amino acid, the linker is preferably a N-PG-amido-PEG$_x$-acid where PG is a protecting group such as the Fmoc group, the BOC group, the CBZ group or any other group amenable to peptide synthesis and X is 2, 4, 6, 8, 12, 24 or any other discrete PEG which may be available. In some embodiments, amino acids may serve as linkers to project a cell binding region of a polypeptide away from the surface of the microcarrier In various embodiments, a 1 μM-2500 μM polypeptide fluid composition, such as a solution, suspension, or the like, is contacted with an activated microcarriers to conjugate the polypeptide. For example the polypeptide concentration may be between about 100 μM and about 2000 μM, between about 500 μM and about 1500 μM, or about 1000 μM. It will be understood that the volume of the polypeptide composition and the concentration may be varied to achieve a desired density of polypeptide conjugated to the microcarrier.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a di-sulfide linkage may be created between free sulfhydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3):502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd.

C. Blocking Carboxylic Groups by Derivation

Following grafting of the polypeptide to the microcarrier base, remaining unconjugated carboxylic acid functional groups (or a portion thereof) of the base may be blocked. For example, the carboxylic acid groups may be blocked via derivitization with a monoamine. Such blocking converts highly hydrophilic carboxylic acid groups to less hydrophilic amide group, which decreases the hydrophilicity of the microcarrier. As a consequence the blocking may alter the cell response to the microcarrier.

If EDC/NHS chemistry is used to graft the peptide to the microcarrier base, excess activated ester (resulting from the pendant COOH moieties) of the microcarrier base can be readily deactivated via monoamine blocking to produce a resulting amide. Of course, blocking by derivitization may be performed in any suitable manner.

Any suitable low molecular weight monoamine may be used for blocking the carboxylic acid groups. Examples of suitable monoamines that may be used include ammonia, hydroxylamine, methylamine, ethyl amine, ethanolamine, methoxyethylamine, n-propylamine, isopropylamine, hydroxyl-propylamine, butylamine, tert-butylamine, sec-butylamine, and the like.

Blocking of the carboxylic acid groups by reaction with excess monoamine typically reduces the number of carboxylic acid groups by about 2 fold to about 4 fold. Complete blocking is generally not achieved due to hydrolysis during blocking. Accordingly, the surface of the microcarrier (without accounting for the polypeptide) tends to remain slightly negative (at physiological, cell culture pH). However, blocking conditions may be adjusted to increase or decrease the efficiency of blocking as desired.

Following blocking, the surface of the microcarrier (except for perhaps portions of the conjugated polypeptide) may be free of positive charge at cell culture pH, and would be neutral or negatively charged. While not intending to be bound by theory, it is believed that the negative charge, or at least the lack of positive charge, would repel cells from the surface in the absence of serum. This could lead to decreased or minimal non-specific binding of cultured cells to the microcarrier base surface so that biospecific interaction between the conjugated polypeptide and cell receptors drive the interaction between the cells and the microcarriers. The reduction of non-specific binding allows for the interaction to be controlled, which can result in better reproducibility of results, such a cellular differentiation or the lack thereof.

2. Cell Culture Articles

Microcarriers as described herein may be used in any suitable cell culture system. Typically microcarriers and cell culture media are placed in a suitable cell culture article and the microcarriers are stirred or mixed in the media. Suitable cell culture articles include bioreactors, such as the WAVE BIOREACTOR® (Invitrogen), single and multi-well plates, such as 6, 12, 96, 384, and 1536 well plates, jars, petri dishes, flasks, multi-layered flasks, beakers, plates, roller bottles, tubes, bags, membranes, cups, spinner bottles, perfusion chambers, bioreactors, CellSTACK® culture chambers (Corning Incorporated) and fermenters.

3. Incubating Cells in Culture Media Having Microcarriers Containing Conjugated Polypeptide A cell culture article housing culture media containing conjugated polypeptide as described above may be seeded with cells. The cells may be of any cell type. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. In various embodiments, the microcarrier with conjugated polypeptide supports undifferentiated culture of embryonic stem cells for 5 or more passages, 7 or more passages, or 10 or more passages. Typically stems cells are passaged to a new surface after they reach about 75% confluency. The time for cells to reach 75% confluency is dependent on media, seeding density and other factors as know to those in the art.

Because human embryonic stem cells (hESC) have the ability to grown continually in culture in an undifferentiated state, the hESC for use with microcarriers as described herein may be obtained from an established cell line. Examples of human embryonic stem cell lines that have been established include, but are not limited to, BG01V/hOG (Invitrogen), H1, H7, H9, H13 or H14 (available from WiCell established by the University of Wisconsin) (Thompson (1998) *Science* 282:1145); hESBGN-01, hES-BGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318:5858).

To maintain stem cells in an undifferentiated state it may be desirable to minimize non-specific interaction or attachment of the cells with the surface of the microcarrier, while obtaining selective attachment to the polypeptide(s) attached to the surface. The ability of stem cells to attach to the surface of a microcarrier without conjugated polypeptide may be tested prior to conjugating polypeptide to determine whether the microcarrier provides for little to no non-specific interaction or attachment of stem cells. Once a suitable microcarrier has been selected, cells may be seeded in culture medium containing the microcarriers.

Prior to seeding cells, the cells may be harvested and suspended in a suitable medium, such as a growth medium in which the cells are to be cultured once seeded. For example, the cells may be suspended in and cultured in a serum-containing medium, a conditioned medium, or a chemically-defined medium. As used herein, "chemically-defined medium" means cell culture media that contains no components of unknown composition. Chemically defined cell culture media may, in various embodiments, contain no proteins, hydrosylates, or peptides of unknown composition. In some embodiments, chemically defined media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, Xvivo (Lonza), and Stem Cell Technologies, Inc. as mTeSR™1 maintenance media for human embryonic stem cells.

One or more growth or other factors may be added to the medium in which cells are incubated with the microcarriers conjugated to polypeptide. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-$\beta$1 (TGF$\beta$1), and colony stimulating factors.

The cells may be seeded at any suitable concentration. Typically, the cells are seeded at about 10,000 cells/cm$^2$ of microcarrier to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are cultured with the microcarriers may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, (vi) for studying drug and toxicity screening, and (vii) the like.

One suitable way to determine whether cells are undifferentiated is to determine the presence of the OCT4 marker. In various embodiments, the undifferentiated stems cells cultured on microcarriers as described herein for 5, 7, or 10 or more passages retain the ability to be differentiated.

In an aspect (6) a microcarrier for cell culture, consisting essentially of: a polystyrene microcarrier base having one or both of (i) a pendant carboxylic acid group, and (ii) one or more pendant amides formed from reaction of carboxylic acid groups with one or more monoamine; and one or more polypeptides conjugated to the base via an amide bond formed from the reaction of an amine of the polypeptide and pendant carboxylic acid group of the microcarrier base is provided. In an aspect (7) a microcarrier according to aspect 6, wherein the carboxylic acid groups or the groups formed from reaction with a carboxylic acid group are extended from a surface of the base via a linker having a chain length of 1 to 15 is provided. In an aspect (8) a microcarrier according to aspect 6 or 7 is provided, wherein the microcarrier base, prior to conjugation with the polypeptide, has a carboxylic acid functional group density of between 0.1 millimoles per gram of the microcarrier base and 1 millimole per gram. In an aspect (9) a microcarrier according to any of aspects 6-8 is provided, wherein the microcarrier base has a surface and wherein the residues of the carboxylic acid extend from the surface via a linker having a chain length of 1 to 15. In an aspect a microcarrier according to any of aspects 6-9 is provided, wherein the cell attachment polypeptide comprises an amino acid sequence of RGD. In an aspect (11) a microcarrier according to any of aspects 6-9 is provided, wherein the synthetic cell attachment polypeptide is selected from the group consisting of a BSP polypeptide, a vitronectin polypeptide, and a fibronectin polypeptide.

In a further aspect (12) a method of making a microcarrier for cell culture, comprising: providing a polystyrene microcarrier base having pendant carboxylic acid functional groups; and conjugating a polypeptide to a carboxylic acid group of a microcarrier base to form the microcarrier. In an aspect (13) a method according to aspect 12 is provided, further comprising blocking at least some of the carboxylic acid functional groups with a monoamine to form an amide. In an aspect (14) a method according to aspect 12 or 13 is provided, wherein the carboxylic acid groups are extended from a surface of the microcarrier base via a linker having a chain length of 1 to 15. In an aspect (15) a method according any of aspects 12-14, wherein the polypeptide comprises an amino acid sequence of RGD is provided. In an aspect (16) a method according to any of claims 12-14 is provided, wherein the polypeptide is selected from the group consisting of a BSP polypeptide, a vitronectin polypeptide, and a fibronectin polypeptide.

In an aspect (17) a method for culturing cells, comprising: contacting cells with a cell culture medium having microcarriers, wherein the microcarrier comprises a polystyrene microcarrier base having residues of carboxylic acid functional groups; and a polypeptide conjugated to the base via the residue of the carboxylic acid functional group; and culturing the cells in the medium is provided. In an aspect (18) the method of aspect 17 is provided, wherein the cells are stem cells and the medium is a chemically defined medium.

In the following, non-limiting examples are presented, which describe various embodiments of the microcarriers and methods discussed above.

EXAMPLES

Example 1

Vitronectin (VN) Conjugation to Polystyrene Beads 100 mg of the COOH functionalized polystyrene microspheres (see Table 1 below for linkers used) were transferred to a 2 mL centrifuge tube, 0.4 g of EDC and 0.1 g of NHS was dissolved in 20 mL of DMF to prepare a stock solution. An aliquot of the solution was added and then allowed to mix on an orbital shaker for 60 min. The solution was aspirated, rinsed once with DMF, aspirated and then an aliquot of the following sequence peptide solution [Ac-Lys-Gly-Gly-Pro-Gln-Val-Thr-Arg-Gly-Asp-Val-Phe-Thr-Met-Pro-NH2] (10 mM in borate buffer, pH 9.2, 0.25% Rhodamine peptide spiked) was added and allowed mix for 60 mM. The peptide solution was removed by aspiration and the spheres were treated with 1.5 mL of 1M ethanolamine pH 8 for 10 min followed by washing with PBS (1.5 mL×5), 1% SDS (1×1.5 mL×1.5 min), DI Water (1.5 mL×5), ethanol (1.5 mL×5) and dried under a gentle stream of nitrogen. Vitronectin conjugated to beads, identified in Table 1 are identified as "Product Code-VN." For example, 555177-VN is the vitronectin-conjugated 555177 product.

TABLE 1

Polystyrene microsphere bases used

| Product Code | Functional Group | Size (microns) | COOH density (mmol/g) |
|---|---|---|---|
| 555177 | ~COOH | 274 | 1.38 |
| 538620 | ~CH2—CH2—COOH | 104 | 1.15 |
| 532371 | ~COOH | 104 | 1 |
| 81536 | ~CH2—CH2—NH—CO—CH2—CH2—COOH | 180 | 1 |
| 81546 | ~CH2—COOH | 104 | 1 |
| 86358 | ~CH2—CH2—O—CH2—CH2—NH—CO—CH2—CH2—COOH | 130 | 0.25 |
| 86333 | ~CH2—CH2—O—CH2—CH2—NH—CO—CH2—CH2—COOH | 110 | 0.4 |

Example 2

Cell Culture with HT1080 Cells

HT1080 cells (ATCC) were routinely expanded on TCT flasks (Corning, N.Y.) in Iscove's Modified Dulbecco's Medium (IMDM) with 10% Fetal Bovine Serum (FBS). For cell adhesion assay, cells were trypsinized and allowed to recover in Iscove's Modified Dulbecco's Medium (IMDM) with 10% Fetal Bovine Serum (FBS) for 30 minutes at 37° C., 5% $CO_2$. After recovery, the cells were washed and resuspended in 0.1% Bovine Serum Albumin (BSA) in IMDM. Approximately 10 mg of peptide derivatized microcarriers were transferred to a 2 mL centrifuge tube and blocked with 2 mL of 1% BSA in D-PBS for 1 hr at room temperature. The microcarriers were then aspiration washed with 2 mL of D-PBS and incubated with 2 mL of 0.1% BSA in IMDM prior to cell seeding. 2 mL of re-suspended cells (200 000 cells/well) were placed in several wells of a 24 well Corning Ultra low attachment microplate. To each cell seeded well was added approximately 10 mg of peptide coated microcarriers and the suspension was incubated for 1 hr at 37 C, 5% $CO_2$. The media was removed and the microcarriers were aspiration washed in the wells with D-PBS (2×2 mL). Cellular attachment and spreading was assessed using Ziess Axiovert 200M inverted microscope.

For cell attachment quantification, D-PBS was removed and 200 ul of Cell Titer-Glo® Reagent (Promega) was added to the microcarriers in the 24 well microplate. Microplate was mixed on an orbital shaker for 10 minutes at room temperature to induce cell lysis. Luminescence was then measured.

Figure 2:
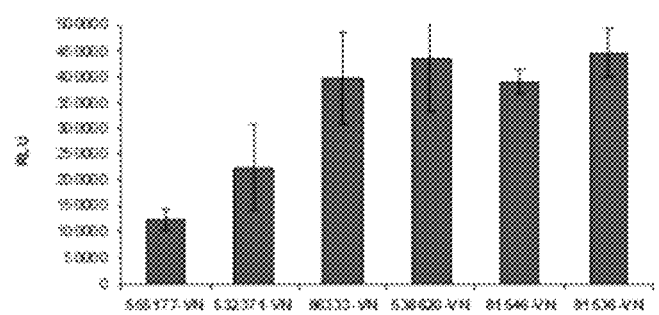
FIG. 2 shows a bar graph of quantification HT1080 cell adhesion based on luminescence reading.

As shown in FIG. 1 all the Vitronectin-conjugated beads tested support short term strong adhesion and spreading of HT-1080 cells. A modified HT-1080 cell adhesion assay was developed to quantify the performance of the beads for cell adhesion (as described above). As shown in FIG. 2 except for beads 555177-VN and 532371-VN, overall all the beads support a very strong HT1080 cell adhesion. This, the presence of a linker between the surface of the bead and the carboxylate group may improve cell adhesion.

Example 3

Cell Culture with ReNcell VM Cells

ReNcell VM cells, human neural progenitor cells, from Millipore (Temecula, Calif.) were routinely expanded on laminin coated T75 cm$^2$ tissue culture flasks (Corning, N.Y.) in ReNcell NSC Maintenance Medium (Millipore, Temecula, Calif.) containing 20 ng/mL FGF-2 and 20 ng/mL EGF (Millipore, Temecula, Calif.). For maintenance and growth of undifferentiated cells, the medium was changed every day. All cells in culture were maintained at 37° C. in a humidified atmosphere of 95% air/5% $CO_2$. Cells were passaged once a week using Accutase™ (Millipore, Temecula, Calif.). For cell adhesion assay, undifferentiated cells were detached by treatment with accutase and allowed to recover in ReNcell NSC Maintenance Medium for 30 minutes at 37° C., 5% $CO_2$. After recovery, the cells were washed and resuspended in 0.1% Bovine Serum Albumin (BSA) in ReNcell NSC Maintenance Medium. Approximately 10 mg of peptide derivatized microcarriers were transferred to a 2 mL centrifuge tube and blocked with 2 mL of 1% BSA in D-PBS for 1 hr at room temperature. The microcarriers were then aspiration washed with 2 mL of D-PBS and incubated with 2 mL of 0.1% BSA in ReNcell NSC Maintenance Medium prior to cell seeding. 2 mL of re-suspended cells (200 000 cells/well) were placed in several wells of a 24 well Corning Ultra low attachment microplate. To each cell seeded well was added approximately 10 mg of peptide coated microcarriers and the suspension was incubated for 1 hr at 37 C, 5% $CO_2$. The media was removed and the spheres were aspiration washed in the wells with D-PBS (2×2 mL). Cellular attachment and spreading was assessed using Ziess Axiovert 200M inverted microscope. For cell attachment quantification, D-PBS was removed and cells on microspheres, 200 ul of Cell Titer-Glo® Reagent (Promega) was added an the microsphere suspension was mixed on an orbital shaker for 10 minutes at room temperature to induce cell lysis. Luminescence was then measured.

Typical surfaces for culture of stem cells consist of poly(styrene) with either a passively adsorbed animal-derived extracellular matrix (ECM) protein or a "feeder" layer of mammalian cells. In particular, the ECM component laminin is a large, posttranslationally modified protein (850 kDa) that is difficult to produce via recombinant expression systems and thus is commonly purified from mammalian cell lines. In addition, human laminin, such as for human embryonic stem cell propagation, is particularly problematic due to significant source variability. Finally, the functions of different cell-binding motifs of laminin and other ECM components have only been partially characterized in select cell lines and are largely unknown for many stem cell lines. Multipotent neural stem cells (NSCs) derived from the adult brain are potentially attractive for neuroregeneration therapies. Natural ECM molecules such as laminin, collagen, and vitronectin have been described to modulate NSC growth rates in vitro. In vitro, NSCs are often propagated in adherent culture on surfaces coated with laminin-1. As cell dependent on ECM component to attach and propagate in vitro, neural stem cells are good model to test the Vitronectin grafted beads described herein.

Figure 3:
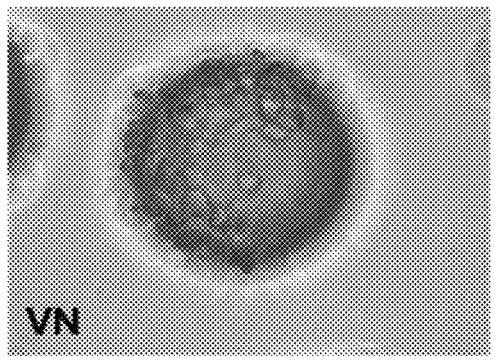
FIG. 3 shows images of undifferentiated neuronal stem cells (ReNcell) adhered to polystyrene microcarriers having conjugated vitronectin peptide (VN) or not bound to scrambled VN peptide (VN-SCB).
Figure 3:
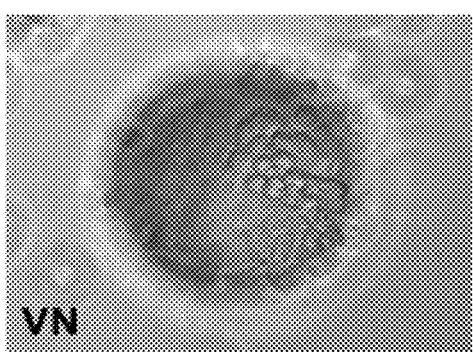
Figure 3:
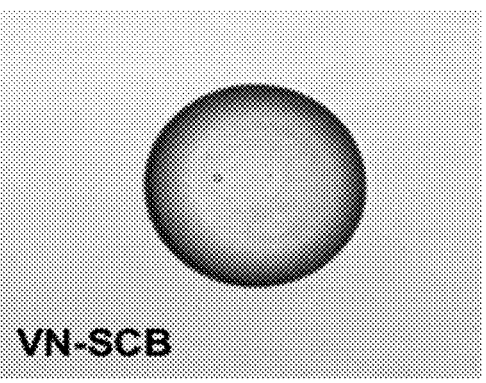
Figure 3:
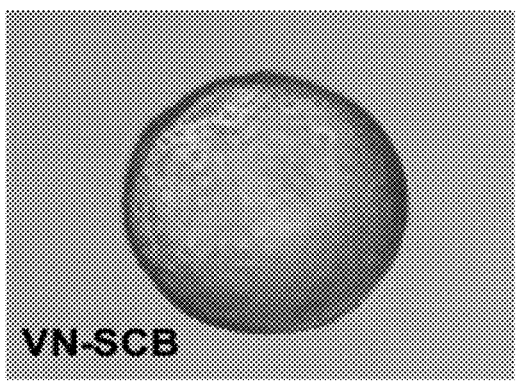
Figure 4:
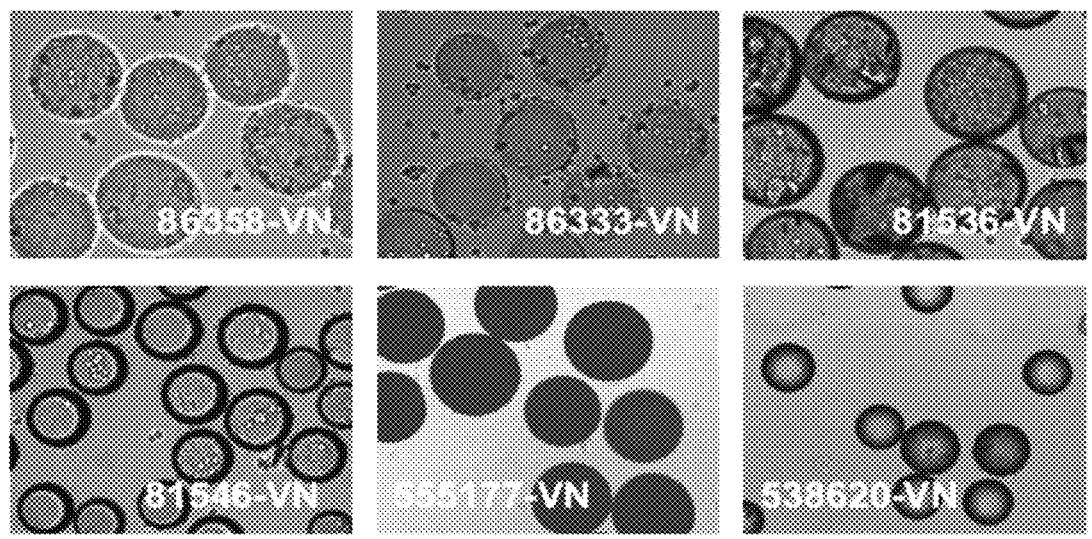
FIG. 4 shows images of neuronal stem cells (ReNcell) bound to polystyrene microcarriers having various length linkers and vitronectin (VN) peptide concentration.
Figure 5:
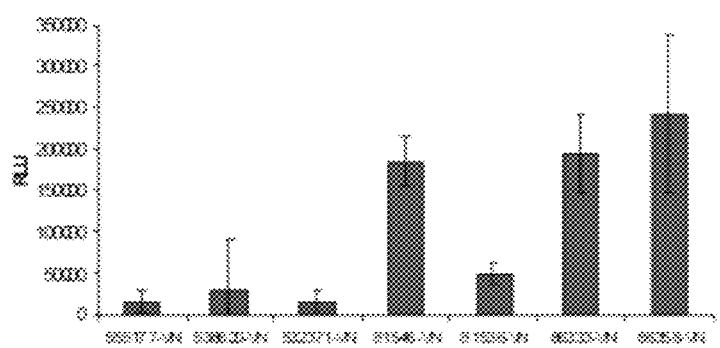
FIG. 5 is a bar graph of quantification ReNcell cells adhesion based on luminescence reading.

As previously described for HT1080 cells, cell adhesion assay was carried with polystyrene beads derivatized with VN peptides (FIGS. 3 and 4). Cell attachment and spreading was assessed using Ziess Axiovert 200M inverted microscope. As shown in FIG. 3, polystyrene beads grafted with VN peptide support short term strong adhesion and spreading of neural stem cells. Neural stem cell attachment was specific to the recognition of the RGD motif on the peptide. Indeed, cells did not attached on surfaces conjugated with the "RGD scrambled" (identified in FIG. 3 as VN-SCB) VN sequence Ac-KGGPQVTGRDVFTMP-NH2 (FIG. 2, VN-SCB), suggesting that the binding is peptide-specific and that non-specific binding to the bead did not occur in any appreciable amount. A modified cell adhesion assay was developed to quantify the performance of the beads for cell adhesion (as described above). As shown in FIG. 4, significant differences in cell adhesion among various beads (with different levels of surface carboxyl groups and different spacer lengths) were observed. This variability is show in the assay results shown in FIG. 5. A very good cell adhesion was seen with long spacer lengths and low concentration of COOH functionality.

Example 4 hES Cells Adhesion and Growth on Microcarriers

As a standard, polystyrene beads (Sigma) were coated over night at 4 C under constant agitation with GFR-Matrigel. Prior the assay the beads were decanted, Matrigel in solution was removed, and the beads were resuspended in mTERS1 medium.

BG01V/hOG cells (Invitrogen) were maintained on Matrigel coated TCT 75 Flask (Corning) in serum free mTERS1 medium containing 50 microgram/ml Hygromycin B (STEMCELL Technologie). Daily medium changes began after the first 48 h in culture. Cells were passaged every 5 to 6 days using collagenase IV (Invitrogen) and mechanical scraping. For the assay, aggregate colonies were harvested and resuspended in fresh mTERS1 medium. Cells were seeded to the 24 wells Corning Ultra low attachment microplate (1.5×10$^5$ cells per cm$^2$) containing the VN-conjugated microcarriers prepared as described above in EXAMPLE 1 or Cytodex™ 3 microcarrier available from GE Healthcare as a comparative example. The volume was adjusted to 600 microliters with culture medium. Cells were allowed to attach to the microcarriers for 48 h without agitation. Two days after seeding, cellular attachment and spreading was assessed using Ziess Axiovert 200M inverted microscope. Quantitative analysis was also performed as followed. The media was removed and the beads were washed in the wells with D-PBS (2×3 mL). The D-PBS was removed and replaced with 200 microliters of CellTiter-Glo reagent (Promega). Microplate was placed in the shaker for 10 min at room temperature and luminescence was measured. For the cell expansion assay, same seeding protocol was used and cells were maintained in static condition over the course of cell expansion. After 48 h cell attachment, culture medium was changed daily after sedimentation of the cells and the beads. After 5 days, cell spreading and cell quantification was assessed using the same methods describe above.

Figure 6:
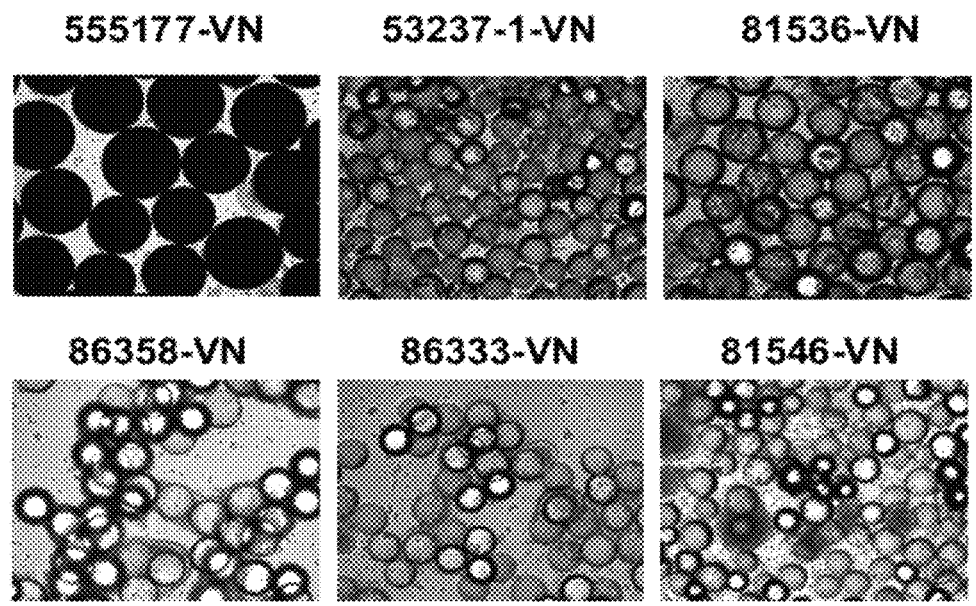
FIG. 6 shows microscopy images of BG01 V/hOG cells growth on Vitronectin peptide grafted PS—COOH microcarriers 2 days after cells seeding.

FIG. 6 shows a microscopy image of BG01V/hOG cells growth on Vitronectin (VN) peptide grafted PS—COOH microcarriers 2 days after cells seeding. As shown in FIG. 6, polystyrene beads grafted with VN peptide support short term strong adhesion and spreading of human embryonic stem cells. hES cell attachment was specific to the recognition of the RGD motif on the peptide and cells did not attach on surfaces conjugated with the "RGD scrambled" VN sequence Ac-KGGPQVTGRDVFTMP-NH2 (data not shown), suggesting that the binding is peptide-specific and that non-specific binding to the bead did not occur in any appreciable amount.

Figure 7:
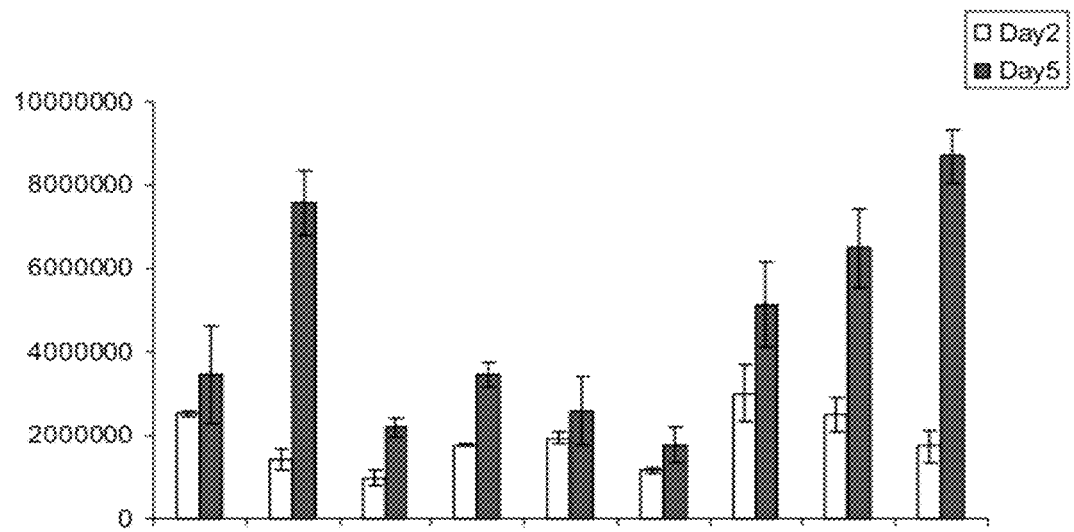
FIG. 7 is a graph showing quantification of BG01V/hOG cells after 2 days and 5 days culture performed on peptide grafted PS—COOH microcarriers, on Matrigel coated beads (Matrigel™ CM) and Cytodex™ 3 as comparative example.

FIG. 7 is a graph showing quantification of BG01V/hOG cells after 2 days and 5 days culture performed on peptide grafted PS—COOH microcarriers, on Matrigel coated beads (Matrigel™ CM) and Cytodex™ 3 as comparative example. The graph is showing clearly the advantage provide by two of the microcarrier of the invention (86333-VN and 86358-VN) after 5 days culture over collagen coated microcarrier from the prior art which do not support BG01V/hOG cell adhesion. Furthermore, this graph shows also that the VN-conjugated microcarriers described herein (86333-VN and 86358-VN) performed as well as the Matrigel coated beads, which have been considered to be the gold standard for culture of human embryonic stem cells.

lengths) supported attachment of HT1080 cells much better than microspheres with no linkers between the surface and the COOH group. In addition, the microspheres having lower COOH density (see Table 1 above for COOH density), and presumably lower polypeptide density, better supported short term adhesion of ReNcells.

The ReNcell data is useful in predicting how well embryonic stem cells may bind to microspheres as described herein. As described in Table 2, hES and ReNcell cells behavior and attachment were identical.

TABLE 2

Summary of Cell Adhesion

| Product Code | HT1080 Short Term Adhesion (luminescence) | ReNcell Short Term Adhesion | hES cell Adhesion |
| --- | --- | --- | --- |
| 555177 | 123175.5 | +/− | − |
| 538620 | 434121.5 | +/− | − |
| 532371 | 224428.5 | +/− | − |
| 81536 | 445772.0 | + | − |
| 81546 | 390715.5 | +++ | ++ |
| 86358 | No data | ++++ | ++++ |
| 86333 | 397108.5 | ++++ | ++++ |

Thus, embodiments of High Surface Area Substrate for Cell Culture are disclosed. One skilled in the art will appreciate that the microcarriers and methods described herein can be practiced with embodiments other than those disclosed. The disclosed embodiments are presented for purposes of illustration and not limitation.

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial sequence
<220> FEATURE:
<223> OTHER INFORMATION: Synthetic Peptide

<400> SEQUENCE: 1

Lys Gly Gly Pro Gln Val Phe Arg Gly Asp Val Phe Thr Met Pro
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic Peptide

<400> SEQUENCE: 2

Lys Gly Gly Pro Gln Val Thr Gly Arg Asp Val Phe Thr Met Pro
1               5                   10                  15
```

SUMMARY OF EXAMPLES

The cell adhesion data for HT1080 cells, ReNcell cells and hES cells (BG01V/hOG) are shown below in Table 2. A few general trends that appear from the data presented in Table 2 are that the presence of a linker appears to improve cell binding and that lower COOH density on the beads supports better adhesion. For example, microspheres having a 2, 6 or 9 chain length linker (see Table 1 above for linker

What is claimed is:

1. A microcarrier for cell culture, comprising:
    a polystyrene microcarrier base having a surface having a net neutral or negative charge at cell culture pH; and
    a polypeptide comprising a cell adhesion sequence covalently attached to the microcarrier base, wherein the cell adhesion sequences comprises RGD.

2. A microcarrier according to claim 1, wherein the microcarrier base, prior to attachment of the polypeptide, has a carboxylic acid functional group density of between 0.1 millimoles per gram and 1 millimole per gram of the microcarrier base, wherein the carboxylic acid functional group density is provided by terminal carbons of moieties covalently attached to the polystyrene microcarrier base, and wherein the polypeptide is covalently attached to the microcarrier base via an amide bond with a carbon of a terminal carbon.

3. A microcarrier according to claim 2, wherein the terminal carbon to which the polypeptide is attached extends from the surface of the microcarrier base via a linker having a chain length of 1 to 15 elements.

4. A microcarrier according to claim 1, wherein the cell adhesion sequence is derived from a BSP polypeptide, a vitronectin polypeptide, or a fibronectin polypeptide.

5. A microcarrier for cell culture, consisting essentially of:
a polystyrene microcarrier base having a surface having one or both of (i) a pendant carboxylic acid group, and (ii) a pendant amide group, wherein the surface of the microcarrier base has a net neutral or negative charge at cell culture pH; and
one or more polypeptides comprising a cell adhesion sequence covalently attached to the base, wherein the cell adhesion sequences comprises RGD;
wherein the microcarrier, at cell culture pH, is free of positively charged moieties or is free of positively charged moieties except for positively charged moieties of the one or more polypeptides.

6. A microcarrier according to claim 5, wherein the carboxylic acid group, if present, the amide group, if present, and the one or more polypeptides extended from the surface of the base via a linker having a chain length of 1 to 15 elements.

7. A microcarrier according to claim 5, wherein the microcarrier base, prior to attachment of the polypeptide, has a carboxylic acid functional group density of between 0.1 millimoles per gram and 1 millimole per gram of the microcarrier base, and wherein the polypeptide is conjugated to the microcarrier base via a residue of a carboxylic acid functional group.

8. A microcarrier according claim 5, wherein the cell adhesion sequence is derived from a BSP polypeptide, a vitronectin polypeptide, or a fibronectin polypeptide.

9. A method of making a microcarrier for cell culture, consisting essentially of:
providing a polystyrene microcarrier base having a plurality of pendant moieties having terminal carbons providing carboxylic acid functional groups; and
covalently attaching one or more polypeptides, each comprising a cell adhesion sequence to at least some of the terminal carbons of the plurality of carboxylic acid groups of the microcarrier base to form the microcarrier,
wherein the cell adhesion sequence of the one or more polypeptides comprises RGD;
wherein the microcarrier, at cell culture pH, is free of positively charged moieties or is free of positively charged moieties except for positively charged moieties of the one or more polypeptides.

10. A method according to claim 9, further comprising blocking at least some of the plurality of carboxylic acid functional groups with a monoamine to form an amide.

11. A method according to claim 9, wherein one or more of the plurality of carboxylic acid groups are extended from a surface of the microcarrier base via a linker having a chain length of 1 to 15 elements.

12. A method according to claim 9, wherein the cell adhesion sequence of each of the one or more polypeptides is derived from a BSP polypeptide, a vitronectin polypeptide, or a fibronectin polypeptide.

13. A method for culturing cells, comprising:
contacting cells with a cell culture medium having microcarriers according to claim 1; and
culturing the cells in the medium.

14. The method of claim 13, wherein the cells are stem cells and the medium is a chemically defined medium.

15. The method of claim 13, wherein the chemically defined medium is a serum-free medium.

16. The method of claim 13, wherein the microcarriers are readily maintained in suspension in the medium.

17. The microcarrier of claim 1, wherein the microcarrier, at cell culture pH, is free of positively charged moieties or is free of positively charged moieties except for positively charged moieties of the one or more polypeptides.

18. The microcarrier of claim 1, wherein the microcarrier has a diametric dimension in a range from 20 microns to 1000 microns.

* * * * *